(12) United States Patent
Schopf et al.

(10) Patent No.: US 6,784,261 B1
(45) Date of Patent: Aug. 31, 2004

(54) IMIDOCHROMIUM COMPOUNDS CONTAINED IN CATALYST SYSTEMS FOR OLEFIN POLYMERIZATION

(75) Inventors: Markus Schopf, Frankfurt (DE); Joerg Sundermeyer, Marburg-Michelbach (DE); Jennifer Kiepke, Marburg (DE); Konstantin A. Rufanov, Leverkusen (DE); Walter Heitz, Kirchhain (DE); Uwe Peucker, Cölbe (DE)

(73) Assignee: Basell Polyolefine GmbH (DE)

( * ) Notice: Subject to any disclaimer, the term of this patent is extended or adjusted under 35 U.S.C. 154(b) by 0 days.

(21) Appl. No.: 10/048,688

(22) PCT Filed: Jul. 25, 2000

(86) PCT No.: PCT/EP00/07103

§ 371 (c)(1),
(2), (4) Date: Apr. 12, 2002

(87) PCT Pub. No.: WO01/09148

PCT Pub. Date: Feb. 8, 2001

(30) Foreign Application Priority Data

Aug. 2, 1999 (DE) .......................... 199 35 592

(51) Int. Cl.[7] .............................. C08F 4/62; C08F 4/622
(52) U.S. Cl. ...................... 526/16; 502/103; 502/167; 526/159; 526/165; 526/161; 526/169
(58) Field of Search .............................. 502/103, 167; 526/159, 165, 161, 169

(56) References Cited

U.S. PATENT DOCUMENTS

| | | | |
|---|---|---|---|
| 3,709,853 A | 1/1973 | Karapinka | 260/88.2 D |
| 4,015,059 A | 3/1977 | Karol | 526/130 |
| 4,404,344 A | 9/1983 | Sinn et al. | 526/160 |
| 5,457,171 A | 10/1995 | Langhauser et al. | 526/132 |
| 5,561,092 A | 10/1996 | Ewen et al. | 502/117 |
| 5,763,549 A | 6/1998 | Elder et al. | 502/110 |
| 5,807,939 A | 9/1998 | Elder et al. | 526/160 |
| 5,883,202 A | 3/1999 | Ewen et al. | 526/124.2 |

FOREIGN PATENT DOCUMENTS

| | | |
|---|---|---|
| EP | 0416815 | 3/1991 |
| EP | 0420436 | 4/1991 |
| EP | 0427697 | 5/1991 |
| EP | 0468537 | 1/1992 |
| EP | 0608447 | 8/1994 |
| EP | 0641804 | 3/1995 |
| EP | 0816384 | 1/1998 |
| WO | 93/16116 | 8/1993 |
| WO | 95/10546 | 4/1995 |
| WO | 97/36937 | 9/1997 |
| WO | 98/03559 | 1/1998 |
| WO | 98/27124 | 6/1998 |

OTHER PUBLICATIONS

Cenini, S., et al, *Inorganica Chimica Acta* 42:65–68, "The Re–action of Molybednum (VI) Dioxo Derivatives with Heterocumulenes," (1980).

Nugent, W. A., et al, "Some Bis(tert–butylimido) Complexes of the Group 6 Transition Metals and a Related Alkylamido Derivative," *Inorg. Chem* 19:777–779 (1980).

Beckert, R., et al, "Sur Chemie der N–Sulfinylverbindungen," *Zeitschrift für Chemie* 22:237–245 (1982).

Nugent, W. A., Synthesis of Some $d^0$.Organoimido Complexes of the Early Transition Metals, *Inorg Chem* 22:965–969 (1983).

Sullivan, A. C., et al, "Synthesis and Reactions of $d^o$ Imido Aryl Derivatives of Chromium, Molybdenum, and Tungsten, Crystal Structures . . . ", *J. Chem Soc. Dalt. Trans.*:53–56 (1988).

Danopoulos, A. A., et al, "t–Butylimido Complexes of Chromium, X–Ray Crystal Structures of $Cr(NBu^1)_2(PMe_2Ph)Cl_2$ and $[Cr(NBu^1)_2(C_5–H_4N)_2(n^1–O_3SCF_3)]O_3SCF_3$," *Polyhedron* 9:2625–2634 (1990).

Meijboom, N., et al, "Organometallic Chemistry of Chromium(VI, Synthesis of Chromium(VI) Alkyls and Their Precursors, X–ray Crystal Structure . . . ", *Organometallics* 9:774–782 (1990).

Leung, W–H, et al, "tert–Butylimido Complexes of Chromium and Vanadium, X–Ray Crystal Structures of $Cr(NBu^r)Cl_3(MeOCH_2CH_2OMe)$, $Cr[6_6H_4(NH)_2–o]Cl_2$. . . ", *J. Chem.Soc.Dalt. .Trans.*:1051–2061 (1991).

Strauss, S. H., "The Search for Larger and More Weakly Coordination Anions," *Chem. Rev.* 93:927–942 (1993).

Coles, M. P., et al, "Well–defined Ethylene Polymerisation Catalysts derived from Bis(imido) Chromium(VI) Precursors," *J. Chem. Soc., Chem. Commun.*:1709–1711 (1995).

"Organometallic Compounds of Cr, Mo and W without Carbonyl Ligands," 5.51.2 Imido complexes through 5.14 References:pp. 291–329 (199_).

Kirk–Othmer, "Olefin Polymers (High Pressure Polyethylene)," In: *Encyclopedia of Chemical Technology*, vol. 9, 1981, pp. 402, 404, 406, 408, 410 and 412.

"Chromium," In: *Compr. Coord. Chem.*, vol. 3, 1987, pp. 935–936.

"Chromium," In: *Compr. Coord. Chem.*, vol. 3, 1987,pp. 938–941.

"Organometallic Compounds of Cr, Mo and W without Carbonyl Ligands", *Comprehensive Organometallic Chemistry II*, vol. 5. 1995, pp. 291–329.

*Primary Examiner*—Caixia Lu
(74) *Attorney, Agent, or Firm*—Connolly Bove Lodge & Hutz LLP

(57) ABSTRACT

The present invention relates to catalyst system containing at least one imidochrome compound and at least one activation compound. This invention also relates to imidochrome compounds, to a method for olefin polymerization and to methods for producing said imidochrome compounds.

8 Claims, No Drawings

IMIDOCHROMIUM COMPOUNDS CONTAINED IN CATALYST SYSTEMS FOR OLEFIN POLYMERIZATION

DESCRIPTION

The subject matter of the present invention is catalyst systems containing imidochromium compounds, new imidochromium complexes, a process for the polymerization of olefins as well as a process for the production of imidochromium complexes.

Many of the catalysts employed for the polymerization of α-olefins are based on immobilized chromium oxides (see, for example, Kirk-Othmer, "Encyclopedia of Chemical Technology", 1981, Volume 16, page 402). Such catalysts generally yield ethylene homopolymers and ethylene copolymers having high molecular weights although they are relatively insensitive to hydrogen, as a result of which they do not allow a simple control of the molecular weight. In contrast, the use of bis(cyclopentadienyl)chromium (U.S. Pat. No. 3,709,853), bis(indenyl)chromium or bis(fluorenyl)chromium (U.S. Pat. No. 4,015,059), which is applied onto an inorganic, oxidic support, makes it possible to easily regulate the molecular weight of polyethylene through the addition of hydrogen.

As is the case with Ziegler-Natta systems, chemists have recently sought for catalyst systems having a uniformly defined, active center, the so-called single-site catalysts, also for chromium compounds. The systematic variation of the ligand skeleton is supposed to make it easy to change the activity, the copolymerization behavior of the catalyst and the properties of the polymers thus obtained.

The preparation of bis(tert.-butylimido)bis(trimethylsiloxy)chromium by means of the reaction of dioxochromium dichloride with tert.-butyl(trimethylsilyl)amine was described by W. Nugent et al. in Inorg. Chem. 1980, 19, pages 777 to 779. Diaryl derivatives of this compound, namely, bis(tert.-butylimido)di(aryl)chromium were prepared by G. Wilkinson et al. as presented in J. Chem. Soc. Dalt. Trans. 1988, pages 53 to 60. The corresponding dialkyl complexes were described for the first time by C. Schaverien et al. (Organomet. 9 (1990), pages 774 to 782). They were also able to isolate a monoimidochromium compound tert.-butylimido(oxo)chromium dichloride by reacting tert.-butyl-imido-bis(trimethylsilanolato)oxochromium with phosphorus pentachloride (W. Nugent in Inorg. Chem. 1983, 22, pages 965 to 969).

EP-A 0,641,804 describes the use of bis(alkylimido)chromium(VI) and bis(arylimido)chromium(VI) complexes for the polymerization of olefins. In EP-A 0,816,384, these bis(imido)chromium(VI) complexes are supported on polyaminostyrene for the polymerization of ethylene and copolymerization of ethylene with higher α-olefins. In this context, the preparation of bis(arylimido)chromium dichloride is a three-stage synthesis route since the reaction of dioxochromium dichloride with N-trimethyl-silylanilines does not yield bis(arylimido)chromium dichloride.

G. Wilkinson et al., were able to prepare tert.-butylimidochromium(V)trichloride and its donor-coordinated derivatives (J. Chem. Soc. Dalt. Trans. 1991, pages 2051 to 2061).

The objective of the present invention was to find new catalyst systems that can be easily modified and that are suitable for the polymerization of α-olefins.

Moreover, the objective was to find an improved synthesis route for the preparation of bis(imido)chromium(VI) compounds.

Accordingly, catalyst systems have been found, containing
(A) at least one imidochromium compound, which can be obtained by a process encompassing the following process steps:
  (a) contacting a dioxochromium compound with an N-sulfinyl compound $R^1$—N=S=O or $R^2$—N=S=O, wherein the variables have the following meaning:
    $R^1$ stands for $C_1$–$C_{20}$-alkyl, $C_2$–$C_{20}$-alkanyl, $C_6$–$C_{20}$-aryl, alkylaryl having 1 to 10 carbon atoms in the alkyl radical and 6 to 20 carbon atoms in the aryl radical, whereby the organic radical $R^1$ can also have inert substituents, for $SiR^3_3$;
    $R^2$ stands for $R^3C$=$NR^4$, $R^2C$=O, $R^3C$=$O(OR^4)$, $R^3C$=S, $(R^3)_2P$=O, $(OR^3)_2P$=O, $SO_2R^3$, $R^5R^4C$=N, $NR^5R^4$ or $BR^3R^4$;
    $R^3$, $R^4$ independent of each other, stand for $C_1$–$C_{20}$-alkyl, $C_2$–$C_{30}$-alkenyl, $C_4$–$C_{30}$-aryl, alkylaryl having 1 to 10 carbon atoms in the alkyl radical and 6 to 20 carbon atoms in the aryl radical, for hydrogen if the latter is bonded to a carbon atom, whereby the organic radicals $R^3$ and $R^4$ can also have inert substituents;
  (b) contacting the reaction product thus obtained with chlorine if a sulfinyl compound $R^1$—N=S=O was used and, in case an N-sulfinyl compound $R^2$—N=S=O was used, with chloride or sulfurylchloride or with no other reagent;
(B) at least one activator compound and
(C) optionally, one or more additional catalysts commonly employed for the polymerization of olefins.

Furthermore, imidochromium compounds having the general formula II,

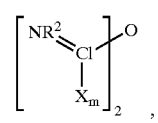

II were found, wherein the variables have the following meaning:
$R^2$ stands for $R^3C$=$NR^4$, $R^3C$=O, $R^3C$=$O(OR^4)$, $R^3C$=S, $(R^3)_2P$=O, $(OR^3)_2P$=O, $SO_2R^2$, $R^3R^4C$=N, $NR^3R^4$ or $BR^3R^4$;
X independent of each other, strands for fluorine, chlorine, bromine, iodine, $NR^5R^6$, $NP(R^5)_3$, $OR^5$, $OSi(R^5)_2$, $SO_3R^5$, $OC(O)R^5$, β-diketonate, sulfate, dicarboxylates, dialcoholates, $BF_4^-$, $PF_6^-$, or bulky weakly on non-coordinating anions;
$R^3$–$R^6$ independent of each other, stand for $C_1$–$C_{20}$-alkyl, $C_2$–$C_{20}$-alkenyl, $C_6$–$C_{20}$-aryl, alkylaryl, having 1 to 10 carbon atoms in the alkyl radical and 6 to 20 carbon atoms in the aryl radical, for hydrogen if the latter is bonded to a carbon atom, whereby the organic radicals $R^3$ and $R^4$ can also have insert substituents;
m is 1 for dianionic X, 2 for monoanionic X.

Imidochromium compounds having the general formula III,

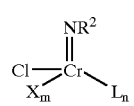

III were likewise found, wherein the variables have the following meaning:

$R^2$ stands for $R^3C=NR^4$, $R^3C=O$, $R^3C=O(OR^4)$, $R^3C=S$, $(R^3)_2P=O$, $(OR^3)_2P=O$, $SO_2R^3$, $R^3R^4C=N$, $NR^3R^4$ or $BR^3R^4$;

X independent of each other, stands for fluorine, chlorine, bromine, iodine, $NR^5R^6$, $NP(R^5)_3$, $OR^5$, $OSi(R^5)_3$, $SO_3R^5$, $OC(O)R^5$, β-diketonate, sulfate, dicarboxylates, dialcoholates, $BF_4^-$, $PF_6^-$, or bulky weakly or non-coordinating anions;

$R^5-R^6$ independent of each other, stand for $C_1-C_{20}$-alkyl, $C_2-C_{20}$-alkenyl, $C_6-C_{20}$-aryl, alkylaryl having 1 to 10 carbon atoms in the alkyl radical and 6 to 20 carbon atoms in the aryl radical, for hydrogen if the latter is bonded to a carbon atom, whereby the organic radicals $R^3$ to $R^6$ can also have insert substituents;

m is 1 for dianionic X, 2 for monoanionic X;
L is a neutral donor;
n is 0 to 3;

Furthermore, a process was found for the production of an imidochromium compound having the general formula IV,

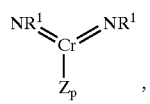

IV wherein the variables have the following meaning:

$R^1$ stands for $C_1-C_{20}$-alkyl, $C_2-C_{20}$-alkenyl, $C_0-C_{20}$-aryl, alkylaryl having 1 to 10 carbon atoms in the alkyl radical and 6 to 20 carbon atoms in the aryl radical, whereby the organic radical $R^1$ can also have inert substituents, or $SiR^3_3$;

Z independent of each other, stands for $C_1-C_{20}$-alkyl, $C_2-C_{20}$-alkenyl, $C_6-C_{20}$-aryl, alkylaryl having 1 to 10 carbon atoms in the alkyl radical and 6 to 20 carbon atoms in the aryl radical, for fluorine, chlorine, bromine, iodine, $NR^5R^6$, $NP(R^5)_3$, $OR^5$, $OSi(R^5)_3$, $SO_3R^5$, $OC(O)R^5$, β-diketonate, sulfate, dicarboxylates, dialcoholates, $BF_4^-$, $PF_6^-$, or bulky weakly or non-coordinating anions;

$R^3$, $R^5$, $R^6$ independent of each other, stand for $C_1-C_{20}$-alkyl, $C_2-C_{20}$-alkenyl, $C_6-C_{20}$-aryl, alkylaryl having 1 to 10 carbon atoms in the alkyl radical and 6 to 20 carbon atoms in the aryl radical, for hydrogen if the latter is bonded to a carbon atom, whereby the organic radicals $R^3$, $R^5$ and $R^6$ can also have inert substituents;

p is 1 for dianionic Z, 2 for monoanionic Z;
characterized in that a dioxochromium compound is reacted with an N-sulfinyl compound $R^1$—NSO.

A process for the production of an imidochromium compound having the general formula I,

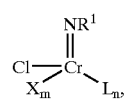

I was likewise found, wherein

X independent of each other, stands for fluorine, chlorine, bromine, iodine, $NR^5R^6$, $NP(R^5)_3$, $OR^5$, $OSi(R^5)_3$, $SO_3R^5$, $OC(O)R^5$, β-diketonate, sulfate, dicarboxylates, dialcoholates, $BF_4^-$, $PF_6^-$, or bulk weakly or non-coordinating anions;

$R^1$ stands for $C_1-C_{20}$-alkyl, $C_2-C_{20}$-alkenyl, $C_6-C_{20}$-aryl, alkylaryl having 1 to 10 carbon atoms in the alkyl radical and 6 to 20 carbon atoms in the aryl radical, whereby the organic radical $R^1$ can also have inert substituents, or $SiR^3_3$;

$R^3$, $R^5$, $R^6$ independent of each other, stand for $C_1-C_{20}$-alkyl, $C_2-C_{20}$-alkenyl, $C_6-C_{20}$-aryl, alkylaryl having 1 to 10 carbon atoms in the alkyl radical and 6 to 20 carbon atoms in the aryl radical, for hydrogen if the latter is bonded to a carbon atom, whereby the organic radicals $R^3$, $R^5$ and $R^6$ can also have inert substituents;

L is a neutral donor;
n is 0 to 3;
m is 1 for dianionic X, 2 for monoanionic X;
characterized in that an imidochromium compound having the general formula V

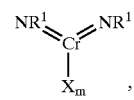

V wherein the variables have the following meaning:

$R^1$ stands for $C_1-C_{20}$-alkyl, $C_2-C_{20}$-alkenyl, $C_6-C_{20}$-aryl, alkylaryl having 1 to 10 carbon atoms in the alkyl radical and 6 to 20 carbon atoms in the aryl radical, whereby the organic radical $R^1$ can also have inert substituents, or $SiR^3_3$;

X independent of each other, stands for fluorine, chlorine, bromine, iodine, $NR^5R^6$, $NP(R^5)_2$, $OR^5$, $OSi(R^5)_3$, $SO_3R^5$, $OC(O)R^3$, β-diketonate, sulfate, dicarboxylates, dialcoholates, $BR_4^-$, $PF_6^-$, or bulky wekly or non-coordinating anions;

$R^5$, $R^5$, $R^6$ independent of each other, stand for $C_1-C_{20}$-alkyl, $C_2-C_{20}$-alkenyl, $C_6-C_{20}$-aryl, alkylaryl having 1 to 10 carbon atoms in the alkyl radical and 6 to 20 carbon atoms in the aryl radical, for hydrogen if the latter is bonded to a carbon atom, whereby the organic radicals $R^3$, $R^5$ and $R^6$ can also have inert substituents;

m is 1 for dianionic X, 2 for monoanionic X;
is reacted with chlorine.

A process for the production of an imidochromium compound having the general formula III,

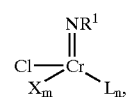

III was likewise found, wherein the variables have the following meaning:

$R^2$ stands for $R^3C=NR^4$, $R^2C=O$, $R^3C=O(OR^4)$, $R^3C=S$ $(R^3)_2P=O$, $(OR^3)_2P=O$, $SO_2R^3$, $R^5R^4C=N$, $NR^3R^4$ or $BR^3R^4$;

X independent of each other, stands for fluorine, chlorine, bromine, iodine, $NR^5R^6$, $NP(R^5)_3$, $OR^5$, $OSi(R^5)_3$, $SO_3R^5$, β-diketonate, sulfate, dicarboxylates, dialcoholates, $BF_4^-$, $PF_6^-$, or bulky weakly or non-coordinating anions;

$R^5-R^6$ independent of each other, stand for $C_1-C_{20}$-alkyl, $C_2-C_{20}$-alkenyl, $C_6-C_{20}$-aryl, alkylaryl having 1 to 10 carbon atoms in the alkyl radical and 6 to 20 carbon atom in the aryl radical, for hydrogen if the latter is bonded to a carbon atom, whereby the organic radicals $R^2$ to $R^6$ can also have inert substituents;

L is a neutral donor;
n is 0 to 3;
m is 1 for dianionic X, 2 for monoanionic X;
characterized in that a dioxochromium compound is reacted with an N-sulfinyl compound $R^2$—N=S=O in the presence of chlorine or sulfurylchloride.

A process for the production of an imidochromium compound having the general formula VI,

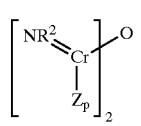

was likewise found, wherein the variables have the following meaning:

$R^2$ stands for $R^3C=NR^4$, $R^3C=O$, $R^3C=O(OR^4)$, $R^3C=S$, $(R^3)_2P=O$, $(OR^3)_2P=O$, $SO_2R^5$, $R^2R^4C=N$, $NR^5R^4$ or $BR^3R^4$;

Z independent of each other, stands for $C_1$–$C_{20}$-alkyl, $C_2$–$C_{20}$-alkenyl, $C_6$–$C_{20}$-aryl, alkylaryl having 1 to 10 carbon atoms in the alkyl radical and 6 to 20 carbon atoms in the aryl radical, for fluorine, chlorine, bromine, iodine, $NR^5R^6$, $NP(R^5)_3$, $OR^5$, $OSi(R^5)_5$, $SO_3R^5$, $OC(O)R^5$, β-diketonate, sulfate, dicarboxylates, dialcoholates, $BF_4^-$, $PF_6^-$, or bulky weakly or non-coordinating anions;

$R^3$–$R^6$ independent of each other, stand for $C_1$–$C_{20}$-alkyl, $C_3$–$C_{20}$-alkenyl, $C_6$–$C_{20}$-aryl, alkylaryl having 1 to 10 carbon atoms in the alkyl radical and 6 to 20 carbon atoms in the aryl radical, for hydrogen if the lamer is bonded to a carbon atom, whereby the organic radicals $R^3$ to $R^6$ can also have inert substituents;

p is 1 for dianionic Z, 2 for monoanionic Z;

characterized in that a dioxochromium compound is reacted with an N-sulfinyl compound $R^2$—NSO.

Furthermore, a process was found for the polymerization of olefins at temperatures within the range from 0° C. to 300° C. [32° F. to 572° F.] and at pressures ranging from 1 bar to 4000 bar, characterized in that the polymerization is carried out in the presence of a catalyst system according to the invention.

The process for the production of the chromium complexes can make use of a wide array of dioxochromium compounds as the starting materials. The important aspect is the presence of the two oxo groups. Other ligands in the chromium starting compound are, among others, the monoanionic and dianionic ligands cited for X and Z. Examples of monoanionic ligands are halogens such as, for instance, fluorine, chlorine, bromine and iodine, amides such as, for instance, dimethylamide, diethylamide and pyrrolidine, alcoholates such as, for example, methanoiate, ethanolate, isopropanolate, butanolate, phenolate and biphenolate, carboxylates such as, for instance, acetate and trifluoracetate, β-diketonates such as, for example, acetylacetonate, dibenzoylmethanate, 1,1,1-trifluoropentane dionate and 1,1,1,5,5,5,-hexafluoropentane dionate, sulfonates such as for instance, toluene sulfonate and trifluoromethane sulfonate, $C_1$–$C_{20}$-alkyl, especially $C_1$–$C_{20}$-alkylsilyls such as, for example, methylene trimethylsilyl, bis-trimethylsilylmethyl, $C_6$–$C_{20}$-aryl such as, for instance, mesityl or weakly or non-coordinating anions. Examples of dianionic ligands are sulfate and chelating dicarboxylates such as, for example, oxalate, fumarate, malonate or succinate and dialcoholates such as, for instance, glycolate. One or more monoanionic or dianionic ligands can be bonded to the dioxochromium compound (also see Compr. Coord. Chem. Vol. 3, G. Wilkinson, Pergamon Press 1987, First Edition, Chapter 35.6.1.3., page 935 and Chapter 35.7.1. through 35.7.2., pages 938 to 941). In addition, one or more neutral donors L can be coordinated on the chromium educts. As a rule, the donor molecules have a heteroatom of the 15th or 16th group of the periodic table of elements. Preference is given to amines, for example, trimethylamine, dimethylamine, N,N-dimethylaniline or pyridine, ethers such as, for instance, tetrahydrofuran, diethylether, dibutylether, dimethoxyethane or dimethyldiethylene glycol, thioethers such as, for example, dimethylsulfide, esters such as, for instance, acetic and methylester, acetic acid ethylester or formic acid ethylester, ketones such as, for instance, acetone, benzophenone or acrolein. Schiff bases, α-diimines, phosphines such as, for example, trimethylphosphine, triethylphosphine or triphenylphosphine, phosphites such as, for instance, trimethylphosphite or triethylphosphite, phosphine oxides, phosphoric acid esters or phosphoric acid amides such as, for example, hexamethylphosphoric acid triamide or N-oxides. The chromium compounds used can be present in a wide array of oxidation stages, preferably from +4 to +6 and especially preferred in the oxidation stage +6. Preferred dioxochromium compounds are dioxochromium dihalides while dioxochromium dichloride is especially preferred.

The N-sulfinyl compounds employed are, for example, N-sulfinylamines for $R^1$—N=S=O, while for $R^3$—N=S=O, they are, for example. N-sulfinylcarbamidines, N-sulfinylcarbamides, N-sulfinylcarbamates, N-sulfinylcarboxylamides, N-sulfinylthiocarboxylamides, N-sulfinylphosphonamides or N-sulfinylsulfonamides. The N-sulfinyl compounds can usually be prepared without problems and, as a rule, in a high yield, from compounds containing $NH_2$ groups and sulfinylation agents such as thionylchloride, sulfur dioxide or else by means of other N-sulfinyl compounds (Z. Chem. [Journal of Chemistry] 22, (1982), pages 235 to 245).

The radicals $R^5$ and $R^4$ are $C_1$–$C_{20}$-alkyl, whereby the alkyl can be linear or branched, such as for example, methyl, ethyl, n-propyl, iso-propyl, n-butyl, iso-butyl, tert.-butyl, n-pentyl, n-hexyl, n-heptyl, n-octyl, n-nonyl, n-decyl or n-dodecyl, five-membered to seven-membered cycloalkyl which, in turn, can have a $C_6$–$C_{10}$-aryl group as the substitutent, such as, for instance, cyclopropane, cycloutane, cyclopentane, cyclohexane, cycloheptane, cyclooctane, cyclononane or cyclododecane, $C_2$–$C_{10}$-alkenyl, whereby the alkenyl can be linear, cyclio or branched and the double bond can be internal or terminal, such as, for instance, vinyl, 1-allyl, 2-allyl, 3-allyl, butenyl, pentenyl, hexenyl, cyclopentenyl, cyclohexenyl, cyclooctanyl or cyclooctadienyl, $C_6$–$C_{20}$-aryl, whereby the aryl radical can be substituted by other alkyl groups such as, for example, phenyl, naphthyl, bi-phenyl, anthranyl, o-methylphenyl, m-methylphenyl, p-methylphenyl, 2,3-dimethylphenyl, 2,4-dimethylphenyl, 2,5-dimethylphenyl or 2,6-dimethylphenyl, 2,3,4-trimethylphenyl, 2,3,5-trimethylphenyl, 2,3,6-trimethylphenyl, 2,4,5-trimethylphenyl, 2,4,6-trimethylphenyl or 3,4,5-trimethylphenyl, or arylalkyl, whereby the arylalkyl can be substituted by other alkyl groups such as, for instance, benzyl, o-methylbenzyl, m-methylbenzyl, p-methylbenzyl, 1-ethylphenyl or 2-ethylphenyl whereby, optionally, two radicals $R^3$ to $R^4$ can also be joined to a five-membered or six-membered ring and/or can also have inert substituents such as halogens, for example, fluorine, chlorine or bromine. Preferred $R^3$ and $R^4$ radicals are hydrogen (if it is bonded to a carbon atom), methyl, ethyl, n-propyl, iso-propyl, n-butyl, iso-butyl, tert.-butyl, tert.-butyl, n-pentyl, n-hexyl, n-heptyl, n-octyl, vinyl, allyl, benzyl, phenyl, ortho-substituted or para-substituted alkyl or chloro-substituted, or bromo-substituted phenyls, ortho, ortho or ortho, paradiakyl-substituted or dichloro-substituted, or dibromo-substituted phenyls, trialkyl-substituted or trichloro-substituted phenyls, fluoro-substituted phenyls, naphthyl, biphenyl and anthranyl. Especially preferred $R^3$ and $R^4$ radicals are methyl, ethyl, n-propyl, iso-propyl, n-butyl, iso-butyl, tert.-butyl, n-pentyl, n-hexyl, n-heptyl, n-octyl, allyl, benzyl, phenyl, 2-chlorophenyl, 2-methylphenyl, 2,6-dimethylphenyl, 2,4-dimethylphenyl, 2,6-diisopropylphenyl, 2,6-dichlorophenyl, 2,4-dichlorophenyl, 2,6-dibromophenyl, 2,4-dibromophenyl, 2,4,6-trimethylphenyl, 2,4,6-trichlorophenyl and pentafluorophenyl.

The $R^1$ radical can be either a C-organic radical, as described above for $R^3$ and $R^4$, or also an Si-organic radical. In the case of the Si-organic substituents $SiR^3_3$, there can also optionally be two $R^3$ joined to a five-membered or six-membered ring and the three $R^3$ radicals can be selected independent of each other such as, for example, trimethylsilyl, triethylsilyl, butyldimethylsilyl, tributylisilyl, triallylallyl, triphenylsilyl or dimethylphenylallyl. Examples of Si-organic substituents are especially trialkylsilyl groups having 1 to 10 carbon atoms in the alkyl radical, particularly triamethylallyl groups. The preferred $R^1$ radical is methyl, ethyl, n-propyl, iso-propyl, n-butyl, iso-butyl, tert.-butyl, n-pentyl, n-hexyl, n-heptyl, n-octyl, vinyl, allyl, benzyl, phenyl, ortho-substituted or para-substituted alkyl or chloro-substituted, or bromo-substituted phenyls, ortho, ortho or ortho, paradialkyl-substituted or dichloro-substituted, or dibromo-substituted phenyls, trialkyl-substituted or trichloro-substituted phenyls, fluoro-substituted phenyls, naphthyl, biphenyl and anthranyl. Especially preferred $R^1$ radicals are benzyl, phenyl, 2-chlorophenyl, 2-methylphenyl, 2,6-dimethylphenyl, 2,4-dimethylphenyl, 2,6-diisopropylphenyl, 2,6-dichlorophenyl, 2,4-dichlorophenyl, 2,6-dibromophenyl, 2,4-dibromophenyl, 2,4,6-trimethylphenyl, 2,4,6-trichlorophenyl, pentafluorophenyl, naphthyl and anthranyl.

$R^2$ can be an imino, isocyanide, formyl, oxo, thioxo, alkoxycarbonyl, aryloxycarbonyl, carbamoyl, phosphinoyl, dialkoxyphosphoryl or diaryloxyphosphoryl, sulfonyl, dialkylamino or diarylamino or dialkylboryl or diaryloryl group. Preferred groups are sulfonyl and oxo, especially arylsulfonyls such as, for instance, toluene sulfonyl, benzene sulfonyl, p-trifluoromethylbenzene sulfonyl or 2,6-diisopropylbenzene sulfonyl and aryloxo such as, for example, benzoyl, 2-methylbenzoyl, 2,6-dimethylbenzoyl, 2,6-diisopropylbenzoyl and 2,4,6-trimethylbenzoyl.

Imidochromium compounds as referred to below are monoimidochromium compounds as well as bis-imidochromium compounds.

The reaction to prepare the imidochromium compound (A) is usually carried out in an inert atmosphere, for example, with nitrogen or argon as the inert gas. Reaction step (a) can be conducted at temperatures between 0° C. and 150° C. [32° F. and 302° F.], preferably between 10° C. and 100° C. [50° F. and 212° F.]. The main solvents used are aprotic solvents such as ethers, for instance, tetrahydrofuran, diethylether, dibutylether, 1,2-dimethoxyethane or diethylene glycol dimethylether, alkanes such as, for example, pentane, n-hexane, iso-hexane, n-heptane, o-octane, cyclohexane or Decalin, aromatic compounds such as, for instance, benzene, toluene or xylene, or chlorohydrocarbons such as methylene chloride, chloroform, tetrachloromethane or dichloroethane. It is also possible to employ solvent mixtures. Preference is given to alkanes and/or chlorohydrocarbons while n-octane and/or tetrachloromethane are especially preferred.

In this context, the reaction product from step (a) can be subjected to the second reaction step either with or without intermediate purification or isolation. The two reaction steps can also be performed simultaneously in one stage. Preferably, the imidochromium complex with $R^1$ is isolated from reaction step (a) before step (b). For imidochromium complexes with $R^2$, step (b) is optional. Therefore, the $R^2$ imidochromium complex can also be mixed with the activator directly, without being contacted with chlorine or sulfuryl-chloride, and then employed in the polymerization. The reaction products from (a) with $R^2$, however, can also be contacted with chlorine or sulfurylchloride and only then be mixed with the activator compound. For $R^2$, steps (a) and (b) are preferably carried out simultaneously as a cone-pot reaction.

The ratio of the dioxochromium compound to the N-sulfinyl compound lies between 1:1 and 1:10, preferably between 1;1 and 1:3 and especially preferred between 1;1 and 1:2.5.

Reaction step (b) can be carried out analogously to the instructions given by G. Wilkinson et al. in J. Chem. Soc. Dalt. Trans. 1991, pages 2051 to 2061 using the reaction product according to (a) instead of bis(tert.-butylimido) chromium dichloride. Sulfurylchloride can be additionally used as the chlorine carrier reagent for $R^2$. The sulfuryl-chloride can be used in an excess to the compound formed from step (a). The ratio of sulfurylchloride to the dioxochromium compound employed can be between 1:1 and 100:1, preferably between 1:1 and 10:1, and especially preferred between 1:1 and 3:1. The reaction is preferably carried out in tetrachloromethane. The reaction temperature here can lie between 0° C. and 100° C. [32° F. and 212° F.], preferably between 10° C. and 60° C. [50° F. and 140° F.] and especially preferred between 20° C. and 60° C. [68° F. and 140° F.].

Special preference is given to catalyst systems in which imidochromium compounds having the general formula I

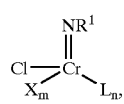

are used, wherein the variable have the following meaning:

X independent of each other, stands for fluorine, chlorine, bromine, iodine, $NR^5R^6$, $NP(R^5)_3$, $OR^5$, $OSi(R^5)_3$, $SO_5R^3$, $OC(O)R^5$, β-dikatonate, sulfate, dicarboxylates, dialcoholates, $BF_4^-$, $PF_6^-$, or bulky weakly or non-coordinating anions;

$R^1$ stands for $C_1$–$C_{20}$-alkyl, $C_2$–$C_{20}$-alkenyl, $C_6$–$C_{20}$-aryl, alkylaryl having 1 to 10 carbon atoms in the alkyl radical and 6 to 20 carbon atoms in the aryl radical, whereby the organic radical $R^1$ can also have inert substituents, or $SiR^3_3$;

$R^3$, $R^5$, $R^6$ independent of each other, stand for $C_1$–$C_{20}$-alkyl, $C_2$–$C_{20}$-alkenyl, $C_6$–$C_{20}$-aryl, alkylaryl having 1 to 10 carbon atoms in the alkyl radical and 6 to 20 carbon atoms in the aryl radical, for hydrogen if the latter is bonded to a carbon atom, whereby the organic radicals $R^3$, $R^5$ and $R^6$ can also have inert substituents;

L is a neutral donor;

n is 0 to 3;

m is 1 for dianionic X, 2 for monoanionic X;

$R^1$ and its preferred embodiments have already been described above. The description of the radicals $R^3$, $R^5$ and $R^6$ is the same as for $R^5$ and $R^4$ elaborated upon above.

The substituents X result from the selection of the appropriate chromium starting compounds that are used for the synthesis of the chromium complexes. Examples of substituents X are, in particular, halogens such as fluorine, chlorine, bromine or iodine, and among these especially chlorine. As additional ligands X, mention should be made of just a few examples, although this is by no means an exhaustive list, namely, $BF_4^-$, $PF_6^-$, as well as weakly or non-coordinating anions (see, for instance, S. Strauss in Chem. Rev. 1993, 93, pages 927 to 942) and also $B(C_6F_5)_4^-$.

Amides, alcoholates, sulfonates, carboxylates and β-diketonates are especially well-suited. By varying the radicals $R^5$ and $R^6$, it is possible, for example, to fine-tune the physical properties, such as the solubility. Preference is given to $C_1$–$C_{10}$-alkyl such as methyl, ethyl, n-propyl, n-butyl, tert.-butyl, n-pentyl, n-hexyl, n-heptyl, n-octyl as well as vinyl, allyl, benzyl and phenyl as the radicals $R^5$ and $R^6$. The use of some of these substituted ligands X is very much preferred since they can obtained from starting materials that are cheap and readily available. For instance, a particularly preferred embodiment is one where X stands for dimethylamide, methanolate, ethanolate, isopropanolate, phenolate, naphtholate, triflate, p-toluene sulfonate, acetate or acetylacetonate. Dianionic ligands of the type described in greater detail above can also be employed. It is particularly preferred if X stands for chlorine and m equals 2. Designating the ligands X as anions does not specify the type of bond to the transition metal. M. For example, if X is a non-coordinating or weakly coordinating anion, then the interaction between the metal M and the ligand X is more of an electrostatic nature. In contrast, in cases where, for instance, X stands for alkyl, the bond is covalent. The various types of bonds are known to the person skilled in the art.

The donor L has also been described above, thereby n corresponds to the number of neutral donor molecules.

The imidochromium compound I can be monomeric or dimeric, or else polymeric. If it is dimeric or polymeric, than one or more ligands on the chromium—this can be X, L or else that imido group—can bridge two chromium centers.

Preferred imidochromium complexes having formula I or III are: methylimidochromium trichloride, ethylimidochromium trichloride, n-propylimidochromium trichloride, isopropylimidochromium trichloride, n-butylimidochromium trichloride, iso-butylimidochromium trichloride, tert-butylimidochromium trichloride, n-pentylimidochromium trichloride, n-hexylimidochromium trichloride, n-heptylimidochromium trichloride, n-octylimidochromium trichloride, allylimidochromium trichloride, benzylimidochromium trichloride, phenylimidochromium trichloride, naphthylimidochromium trichloride, biphenylimidochromium trichloride, anthranylimidochromium trichloride, 2-chlorophenylimidochromium trichloride, 2-methylphenylimidochromium trichloride, 2,6-dimethylphenylimidochromium trichloride, 2,4-dimethylphenylimidochromium trichloride, 2,6-diisopropylphenylimidochromium trichloride, 2,6-dichlorophenylimidochromium trichloride, 2,4-dichlorophenylimidochromium trichloride, 2,6-dibromophenylimidochromium trichloride, 2,4-dibromophenylimidochromium trichloride, 2,4,6-trimethylphenylimidochromium trichloride, 2,4,6-trichlorophenylimidochromium trichloride, pentafluorophenylimidochromium trichloride, trifluoromethylsulfonlimidochromium trichloride, toluene sulfonylimidochromium trichloride, phenylsulfonylimidochromium trichloride, p-trifluoromethylphenylsulfonylimidochromium trichloride, or 2,6-diisopropylphenylsulfonylimidochromium trichloride, formylimidochromium trichloride, acylimidochromium trichloride, benzoylimidochromium trichloride, naphthoylimidochromium trichloride, anthranoylimidochromium trichloride, 2-cyclobenzoylimidochromium trichloride, 2-chlorobenzyolimidochromium trichloride, 2-methylbenzoylimidochromium trichloride, 2,6-dimethylbenzoylimidochromium trichloride, 2,4-dimethylbenzoylimidochromium trichloride, 2,6-diisopropylbenzoylimidochromium trichloride, 2,6-dichlorobenzoylimidochromium trichloride, 2,4-dichlorobenzolylimidochromium trichloride, 2,6-dibromobenzoylimidochromium trichloride, 2,4-dibromobenzoylimidochromium trichloride, 2,4,6-trimethylbenzoylimidochromium trichloride, 2,4,6-trichlorobenzoylimidochromium trichloride or pentafluorobenzoylimidochromium trichloride.

The catalyst systems according to the invention also contain an activator, component (B), which is put in contact with the chromium complex. Examples of activator compounds are those of the alumoxane type (or aluminoxane), especially methyl alumoxane MAO. Alumoxanes are produced, for example, by means of the controlled addition of water or aqueous substances to alkyl aluminum compounds, especially trimethyl aluminum (for example, U.S. Pat. No. 4,404,344). Alumoxane preparations that are suitable as co-catalysts are commercially available. It is assume that this is a mixture of cyclic and linear compounds. The cyclic alumoxanes can be encompassed by the formula $(R^7AlO)$, and the linear aluminoxanes by the formula $R^7(R^7AlO)_2AlR^7_2$, wherein s indicates the degree of oligomerization and it is a number ranging from about 1 to 50. Advantageous alumoxanes contain essentially alumoxane oligomers having a degree of oligomerization of about 2 to 30 and $R^7$ is preferably an $C_1$–$C_4$-alkyl and especially preferably methyl, ethyl, butyl or isobutyl.

In addition to the alumoxanes, possible activator components are those of the type used in the so-called cationic activation of metallocene complexes. Such activator complexes are known, for example, from EP-B 0,468,537 and from EP-B-0,427,697. In particular, boranes, boroxines or borates such as, for instance, trialkyl borane, triaryl horane trimethyl boroxine, dimethyl anilinium tetraaryl borate, trityletraaryl borate, dimethyl anilinium boratabenzenes or trityl boratabenzenes (see WO-A 97/36937) can be employed as such activator compounds (B). Special preference is given to the use of boranes or borates that have at least two perfluorinated aryl radicals.

Activator compounds having strong oxidizing properties can also be used such as, for instance, silver borates, especially silver tetrakispentafluorophenyl borate or ferrocenium borates, especially ferrocenium tetrakispentafluorophenyl borate or ferrocenium tetraphenyl borate.

Compounds such as aluminum alkyls, especially trimethyl aluminum, triethyl aluminum, triisobutyl aluminum, tributyl aluminum, dimethyl aluminum chloride, dimethyl aluminum fluoride, methyl aluminum, dichloride, methyl aluminum sesquichloride, diethyl aluminum chloride or aluminum trifluoride can likewise be employed as activator components. The hydrolysis products of aluminum alkyls with alcohols can also be used (see, for instance, WO-A 95/10546).

Furthermore, alkyl compounds of lithium, magnesium or zinc such as, for example, methyl magnesium chloride, methyl magnesium bromide, ethyl magnesium chloride, ethyl magnesium bromide, butyl magnesium chloride, phenyl magnesium chloride, dimethyl magnesium, diethyl magnesium, dibutyl magnesium, methyl lithium ethyl lithium, methyl zinc chloride, dimethyl zinc or diethyl zinc can be used as activator compounds.

Especially preferred catalyst systems are those in which the activator compound (B) is selected from the following group: aluminoxane, trimethyl aluminum, triethyl aluminum, triisobutyl aluminum, dimethyl aluminum chloride, diethyl aluminum chloride, methyl aluminum dichloride, ethyl aluminum chloride, methyl aluminum sesquichloride, dimethylanilinium tetrakispentafluorophenyl borate, trityltetrakispentafluorophenyl borate or trispentafluorophenyl borane.

Sometimes, it is desirable to make use of a combination of several activators. This is a known procedure, for example, with metallocenes in which boranes, boroxines (WO-A 93/16116) and borates are often used in combination with an aluminum alkyl. Generally speaking, a combination of various activator components with the chromium complexes according to the invention is likewise possible.

The amount of activator compounds to be used depends on the type of activator. Generally speaking, the molar ratio of chromium complex (A) to activator compound (B) can range from 1:0.1 to 1:10,000, preferably from 1:1 to 1:2000. The molar ratio of chromium complex (A) to dimethylanilinium tetrakispentafluorophenyl borate, trityltetrakispentafluorophenyl borate or trispentafluorophenyl borane preferably lies between 1:1 and 1:20, and especially preferred between 1:1 and 1:10, with respect to methyl aluminoxane, preferably between 1:1 and 1:2000 and especially preferred between 1:10 and 1:1000. Since many of the activators such as, for instance, aluminum alkyls are concurrently employed to remove catalyst poison (so-called scavengers), the quantity employed also depends on the purity of the other substances used. The person skilled in the art, however, can determine the optimal amount by means of simple experimentation.

The mixture with the activator compound can be carried out in a wide array of aprotic solvents, preference being given to alkanes such as pentane, hexane, heptane and octane, or to aromatic compounds such as benzene, toluene and xylene, whereby pentane, hexane, heptane and toluene are particularly preferred. Solvent mixtures, especially of alkanes with aromatic compounds, are also advantageous for purposes of adjusting to the solubilities of the catalyst system.

The mixing with the activator compound takes place at temperature between −50° C. and 150° C. [−58° F. and 302° F.], preferably between 10° C. and 50° C. [50° F. and 122° F.], especially preferred between 15° C. and 30° C. [59° F. and 86° F.].

For the polymerization, one or more of the catalyst systems according to the invention can be used simultaneously. As a result, for example, bimodal products can be obtained. A wider product spectrum can also be achieved by using the imidochromium compounds in combination with another polymerization-active catalyst (C). In this context, at least one of the catalyst systems according to the invention is used in the presence of at least one catalyst (c) commonly employed for the polymerization of olefins. Here, preference is given to the use of Ziegler-Natta catalyst on the basis of titanium, classic Phillips catalysts on the basis of chromium oxides, metallocenes, the so-called constrained geometry complexes (see, for instance, EP-A 0,416,815 or EP-A 0,420,436), nickel and palladium bis-imine systems (for their preparation, see WO-A 98/03559), iron and cobalt pyridine-bis-imine compounds (for this preparation, see WO-A 98/27124) or chromium pyrrol compounds (see, for example EP-A 0,608,447) as the catalysts (C). Thus, by means of such combinations, for example, bimodal products can be produced or comonomers can be generated in situ. In this context, depending on the selection of the catalyst, it is advantageous to employ one or more activators. The polymerization catalysts (C) can likewise be on a support and they can be contacted simultaneously or in any desired order with the catalyst system according to the invention or with its components. A pre-activation of the catalyst (C) with an activator compound (B) is likewise possible.

The description and the preferred embodiments of $R^1$ to $R^6$ and for X in the imidochromium compounds II and III as well as in the processes for the production of the chromium complexes I, III, IV and VI, the former employing the imidochromium compound V, are all the same as elaborated upon above. The reaction conditions have largely been described above as well.

Z and its preferred embodiments stand for the same described above for X and additionally also for alkyls or aryls, especially preferred for methylene trimethylsilyl, benzyl or mesityl.

The processes for the production of the chromium complexes III and V are fundamentally carried out under the same conditions, as a result of which the reaction parameters will be described together below.

An essential reaction step is the contacting of the N-sulfinyl compound with the corresponding dioxochromium compound. The dioxochromium compounds have likewise been described above. Here as well, the preferred dioxochromium compound is dioxochromium dichloride. The N-sulfinyl compounds have likewise been described above. The preferred embodiments result from the preferred embodiments of the radicals $R^1$ or $R^2$ of the imido group of the chromium complex being formed (see above). The reaction step has already been described above for the reaction step (a). This can be followed by a regular purification step, for instance, recrystallization or filtration.

The process according to the invention for the polymerization of olefins can be combined with all of the technically known polymerization methods at temperatures within the range from 0° C. to 300° C. [32° F. to 572° F.] and at pressures ranging from 1 bar to 4000 bar. Therefore, the advantageous pressure and temperature ranges at which to carry out the process depend to a great extent on the polymerization method. Thus, the catalyst systems used according to the invention can be employed in all of the known polymerization processes such as, for example, a high-pressure polymerization process in tubular-flow reactors or autoclaves, in suspension-polymerization processes, in solution-polymerization processes or in gas-phase polymerization. In the case of the high-pressure polymerization process, which is normally carried out at pressures between 1000 and 4000 bar, especially between 2000 and 3500 bar, high polymerization temperatures are usually set as well. Advantageous temperature ranges for these high-pressure polymerization processes lie between 200° C. and 300° C. [392° F. and 572° F.]. especially between 220° C. and 270° C. [428° F. and 518° F.]. When it comes to the lower-pressure polymerization process, the selected temperature is usually at least a few degrees below the softening point of the polymer. The polymerization temperature can be between 0° C. and 180° C. [32° F. and 356° F.]. In particular, temperature between 50° C. and 180° C. [122° F. and 356° F.], preferably between 70° C. and 120° C. [158° F. and 248° F.] are set in these polymerization processes. Among the polymerization methods mentioned, preference is given according to the invention to gas-phase polymerization, especially in gas-phase fluidized-bed reactors, as well as to suspension polymerization, particularly in loop-type reactors and stirred-tank reactors as well as to solution polymerization. Gas-phase polymerization can also be performed in the so-called condensed, supercondensed or supercritical mode of operation. Different or else the same polymerization methods can optionally also be connected with each other in series so as to create a polymerization cascade. Moreover, in order to regulate the polymer properties, an additive such as, for instance, hydrogen, can also be used in the polymerization processes.

Using the process according to the invention, various olefinically unsaturated compounds can be polymerized, which also includes copolymerization. In contrast to a few known iron and cobalt complexes, the transition-metal complexes used according to the invention exhibit good polymerization activity, even with higher α-olefins, so that special mention needs to be made of their suitability for copolymerization. Aside from ethylene and α-olefins having 3 to 12 carbon atoms, examples of olefins are also internal olefins and non-conjugated and conjugated dienes such as butadiene, 1,5-hexadiene or 1,6-heptadiene, cyclic olefins such as cyclobutene, cyclopentane or norbornene and polar monomers such as acrylic acid ester, acrolein, acrylonitrile, vinylether, allylether and vinylacetate. Vinyl-aromatic compounds such as styrene can also be polymerized by means of the process according to the invention. Preferably, at least one olefin selected from the group consisting of ethene, propene, 1-butene, 1-pentene, 1-hexene, 1-heptene, 1-octene, cyclopentene and norbornene is polymerized. A preferred embodiment of the process according to the invention is characterized in that mixtures of ethylene with $C_3$–$C_8$-α-olefins are used as the monomers.

In this context, the chromium complex can be brought into contact with the activator compound or compounds either before or after contacting with the olefins to be polymerized. Another possibility is pre-activation with one or more activator compounds prior to mixing with the olefin and the further addition of the same or different activator compounds after this mixture has been contacted with the olefin. As a rule, pre-activation is conducted at temperatures between 10° C. and 100° C. [50° F. and 212° F.], preferably between 20° C. and 80° C. [68° F. and 176° F.].

Furthermore, more than one of the catalyst systems according to the invention can be simultaneously brought into contact with the olefin to be polymerized. This has the advantage that a wide range of polymers can be thus created. In this manner, bimodal products, for example, can be produced.

The catalyst systems according to the invention can optionally also be immobilized on an organic or inorganic support and then be used in the polymerization in this supported form. This is a common method employed to avoid reactor deposits and to regulate the polymer morphology. Preferably support materials are silica gel, magnesium chloride, aluminum oxide, mesoporous materials, alumosilicates and organic polymers such as polyethylene, polypropylene or polystyrene and especially silica gel or magnesium chloride.

One or more of the catalyst systems according to the invention can be immobilized on a support. The components of the catalyst system can be put into contact with the support in varying orders or all at the same time. This is usually done in an inert solvent that can be filtered off or evaporated after the immobilization procedure. The use of the still moist, supported catalyst is also possible. For instance, the support can be first mixed with the activator compound or compounds or else the support can first be contacted with the polymerization catalyst. Pre-activation of the catalyst with one or more activator compounds prior to the mixing with the support is also possible. The amount of chromium complex (A) in mmoles per gram of support material can vary widely, for example, from 0.001 to 1 mmole/g. The preferred quantity of chromium complex (A) per gram of support material lies between 0.001 and 0.5 mmole/g, especially preferably between 0.005 and 0.1 mmole/g. In one possible embodiment, the chromium complex (A) can also be produced in the presence of the support material. Another type of immobilization is the pre-polymerization of the catalyst system with or without a prior supporting step.

Polymers of olefins can be produced by means of the process according to the invention. The term polymerization as employed here to describe the invention comprises both polymerization and oligomerization, that is to say, oligomers and polymers having molecular weights within the range from about 56 to 4,000,000 can be produced by means of this process.

In view of their good mechanical properties, the polymers produced with the catalyst system according to the invention are particularly suitable for the manufacture of films, fibers and molded articles.

The catalysts according to the invention display moderate levels of productivity.

The comparative examples for the bis-imidochromium compounds described in EP-A 0,641,804 show that the monoimide compound according to the invention, ($C_6F_5N$) $CrCl_5$, yielded higher levels of activity. In comparison to the bis-imido compounds, the norbornene polymerization did not yield any metathesis products.

The new process for the production of bis-imidochromium compounds is a one-pot synthesis. In this manner, up to two synthesis steps can be dispensed with in the preparation of bis(arylimido)chromium complexes.

N-sulfinylamines have been employed by S. Chenini and M. Pizzotti (Inorg. Chim. Acta [Inorganic chemical archives] 42, (1980), 65) for the synthesis of molybdenum imido compounds. It was assumed that the released $SO_2$ would reduce the chromium species when the reduction-prone chromium(VI)dioxo-compounds are used. Surprisingly, however, this was not observed.

The examples that follow serve to illustrate the invention.

Unless otherwise indicated, all of the work was performed in the absence of air and moisture. Toluene was dried and distilled off over a molecular sieve column or potassium-benzophenone. Triethyl aluminum (2 M in heptane) and MAO (methyl aluminoxane 30% in toluene) were obtained from the Witco GmbH and Albermarle companies.

Analytical Methods

The elementary analyses were carried out using a Herseus CHN-Rapid unit.

The IR spectra were obtained with a Nicolet 510M as a Nujol trituration between KBr plates.

The η value was determined with an automatic Ubbelohde viscosimeter (Laudar PVS 1) with Decalin as the solvent at 130° C. [266° F.] (ISO 1628 at 130° C. [266° F.], 0.001 g/mL of Decalin).

EI mass spectra were obtained with a Varian MAT CH7 unit.

The melting points were determined by means of a Melting Point B-540 device manufactured by the Buechi company.

The NMR spectra were obtained with a Bruker ARX 200 unit or with a Bruker AMX 300 unit.

Key to the abbreviations used in the following tables:
Cat. ex. Catalyst according to the example
yield yield of polymer
gP grams of polymer
Tg glass transition temperature
Tm melting temperature
h Staudinger index (viscosity)
tBu tert.-butyl
Ts para-toluene sulfone
Bz benzoyl
Tf trifluoromethane sulfone

EXAMPLE 1

Preparation of bis((2,6-diisopropylphenyl)imido) chromium dichloride

A 0.84-molar solution of chromylchloride in $CCl_4$ (455 mg. 2.94 mmoles of $CrO_2Cl_2$) was diluted with 30 mL of octane and slowly mixed with 1.45 g (6.47 mmoles) of (2,6-diisopropylphenyl)sulfinylamine.

The reaction mixture was subsequently heated for 12 hours under reflux, whereby, at certain times, a stream of inert gas was passed through the reaction solution in order to expel the $SO_2$ that was forming. The precipitated brown-violet solid was filtered off, washed with cold pentane and dried in a high vacuum. Yield: 1.22 g (88%) of bis (diisopropylphenylimido)chromium dichloride.

$^1$H-NMR ($C_6D_6$, 200 MHz); δ=1.08 (d 24H $3I_{HH}$=6.8 Hz, CH(CH$_3$)$_2$), 3.86 (sept. 4H, $3I_{MM}$=6.7 Hz, C$\underline{H}$(CH$_3$)$_2$), 6.72 (s, 6H, Ph-$\underline{H}$) ppm.

$^{13}$C-NMR ($C_6D_6$, 50 MHz): δ=23.5 (CH ($\underline{C}H_3$)$_2$), 30.0 ($\underline{C}$H(CH$_3$)$_2$), 123.7 (Ph-$\underline{C}_{(meth)}$), 132.3 (Ph-$\underline{C}_{(para)}$), 148.9 (Ph-$\underline{C}_{(ortho)}$)ppm.

IR (Nujol):≡2855 s, 1642 w, 1582 m. 1296 m, 1262 m, 1221 w, 1142 w, 1080 m(br), 1022 m(br), 912 w, 799 m, 754 w, 721 w, 563 m cm$^{-1}$.

EI-MS: m/z=175 (DipN⁺, 57%), 160 (Dip-H, 71%), 119 ($C_9H_{12}$+25%), 36 (Cl, 100%).
Dip=2,6-diisopropylphenyl
Ph=phenyl

EXAMPLE 2

Preparation of bis(tert.-butylimido)chromium Dichloride

A 0.84-molar solution of chromylchloride in $CCl_4$ (566 mg, 3.67 mmoles of $CrO_2Cl_2$) was diluted with 20 mL of octane and mixed with 963 g (8.08 mmoles) of tert.-butylsulfinylamine. The reaction mixture was subsequently heated for 12 hours under reflux, whereby, at certain times, a stream of inert gas was passed through the reaction solution in order to expel the $SO_2$ that was forming. The precipitated violet solid was filtered off, washed with solid pentane and dried in a high vacuum. Yield: 770 mg (79%) of bis(tert.-butylimido)chromium dichloride.

$^1$H-NMR (CDCl₃, 200 MHz): δ=1.60 (s, 18H, C (C$\underline{H}_3$)₃) ppm.
$^{13}$C-NMR (CDCl₃, 50 MHz): δ=30.2 (C ($\underline{C}H_3$)₃) ppm.

EXAMPLE 3

Preparation of bis((2,4,6-trimethylphenyl)imido) chromium Dichloride

A 0.84-molar solution of chromylchloride in $CCl_4$ (605 mg, 3.92 mmoles of $CrO_2Cl_2$) was diluted with 20 mL of octane and slowly mixed with 1.66 g (8.63 mmoles) of mesitylsulfinylamine. The reaction mixture was subsequently heated for 12 hours under reflux whereby, at certain times, a stream of insert gas was passed through the reaction solution in order to expel the $SO_2$ that was forming. The precipitated red-brown solid was filtered off, washed with cold pentane and dried in a high vacuum. In this manner, bis((2,4,6-trimethylphenyl)imido)chromium dichloride was isolated in a yield of 91%.

$^1$H-NMR ($C_6D_6$, 200 MHz): δ=1.84 (s, 6H, Mes-C $\underline{H}_3)_{(para)}$), 2.25 (s, 12H Mea-C$\underline{H}_5)_{(ortho)}$), 6.23 (s, 4H, Mes-$\underline{H}_{(meth)}$) ppm.

EXAMPLE 4

Preparation of bis(pentafluorophenylimido) chromium Dichloride

A 0.84-molar solution of chromylchloride in $CCl_4$ (3.30 g, 21.4 mmoles of $CrO_2Cl_2$) was diluted with 80 mL of tetrachloromethane and mixed with 10.79 g (47.08 mmoles) of pentafluorophenylsulfinylamine at room temperature. The reaction mixture was subsequently stirred for 4 hours until there was no more gas formation to be seen. During the cooling off phase, a weak stream of inert gas was passed through the reaction solution in order to expel the $SO_2$ that had formed during the reaction. The precipitated dark-red solid was filtered off, washed with cold pentane and dried in a high vacuum. Yield: 95% of bis(pentafluorophenylimido) chromium dichloride.

$^{19}$F-NMR (CDCl₃, 188 MHz): δ=−144.2 (d, 4F, 3$I_{FF}$= 15.3 Hz, Arf-$F_{(ortho)}$), −148.3 (t, 2F, 3$I_{FF}$=20.4 Hz, Arf-$F_{(para)}$), −155.9 (t, 4F, 3$I_{pp}$=20.3 Hz, Arf-$F_{(meth)}$) ppm.

IR (Nujol): ≈1632 s, 1507, ,s 1263 m, 1150 m, 1121 m, 1063 s 997 s, 864 w, 802 w, 721 w, 642 m, 561 m, 440 w cm⁻¹.

Arf=pentafluorophenyl

EXAMPLE 5

Reaction of dioxochromiumdichloride with N-(toluene sulfonyl)sulfinylamide

A 0.84-molar solution of chromylchloride in $CCl_4$ was mixed at room temperature with 2.2 equivalents of sulfinylamide dissolved in tetrachloromethane. Subsequently, the reaction mixture was heated under a reflux until there was no more gas formation to be seen. The resultant brown solid was filtered off, washed with pentane and dried in a high vacuum. Yield: 90%.

Only a sharp signal was observed in the EPR spectrum for this compound.

Means values of the elementary analysis: C 25:31 H 2.37 N 3.28 Cl 22.89 S 12.15 Cr 13.16

EXAMPLE 6

Reaction of Dioxochromiumdichloride with N-(Toluene Sulfonyl)sulfinylamide in the Presence of Chlorine A 0.84-molar solution of chromylchloride in $CCl_4$ was mixed at room temperature with 2.2 equivalents of N-(toluene sulfonyl)sulfinylamide dissolved in tetrachloromethane. A stream of chlorine gas was passed through the reaction solution for 10 minutes. Subsequently, the reaction mixture was heated under a reflux until there was not more gas formation to be seen. During the reaction as well, a weak stream of chlorine gas was passed through the reaction solution. The resultant yellow-brown solid was filtered off, washed with pentane and dried in a high vacuum. The yield was approximately 90%.

As an alternative, instead of chlorine gas, 5 mL of sulfurylchloride can be added to the above-mentioned solution. After agitation for 24 hours at room temperature, the preparation proceeded analogously.

Very wide, weak signals can be observed in the $^1$H-NMR spectrum, which indicates a paramagnetic compound.

EXAMPLES 7 to 9

Reaction of the bis(imido)chromium dichloride with chlorine (analogously to G. Wilkinson et al., in J. Chem. Soc. Dalt. Trans. 1991, pages 2051 to 2061).

These experiments were carried out for complexes having the following radicals on the imido ligands; tert.-butyl (7), 2,6-diisopropylphenyl (8) and pentafluorophenyl (9).

A total of 5 g of bis(imido)chromium dichloride was dissolved in 50 mL of methylene chloride. At room temperature, a stream of chlorine gas was passed through the reaction solution for 10 minutes. Subsequently, the mixture was left standing for one hour at room temperature, after which the volatile components were removed in a vacuum.

These reactions transpired virtually quantitatively.

Elementary analysis:

| (8) | calculated: | C 43.20 | H 5.14 | N 4.20 |
|---|---|---|---|---|
|     | found:      | C 41.60 | H 5.24 | N 5.46 |
| (9) | calculated: | C 21.23 | N 4.13 |        |
|     | found:      | C 21.27 | N 4.25 |        |

EXAMPLE 10

Ethene Polymerization

A total of 0.20 mmole of the chromium compound from Example 5 was dissolved in 61 mL of toluene. The solution was transferred into a 250-mL glass autoclave, where it was first brought to a temperature of 0° C. [32° F.] and subsequently saturated with ethene for 30 minutes at 3 bar. Then the reaction was started by adding 670 mg of MAO (Cr:Al= 1:50) dissolved in 40 mL of toluene. The first polymer particles already precipitated from the reaction solution after a few minutes. After a reaction time of 3 hours, the reaction was interrupted by dripping the polymerization mixture into a mixture of methanol and hydrochloric acid. The polymer precipitate obtained in this process was filtered off. washed with methanol and dried in a vacuum at 100° C. [212° F.]. The yield was 2.3 g of polyethylene having a melting point of 136° C. [276.8° F.] and η=19.

EXAMPLE 11

Norbornene Ethene Copolymerization

First of all, 0.200 mmole of the chromium compound from Example 5 was suspended in 50 mL of toluene. This solution was then put into a 250-mL glass autoclave. Subsequently, 40 mL of a norbornene-toluene solution (318.60 mmoles of norbornene) were added to this solution. The reaction mixture thus obtained was first brought to a temperature of 0° C. [32° F.] and subsequently saturated with ethene for 30 minutes at 3 bar. Then the reaction was started by adding 1.34 g of MAO (Cr:Al=1:50) dissolved in 20 mL of toluene. After a reaction time of 1.5 hours, the reaction was interrupted by dripping the polymerization mixture into a mixture of methanol and hydrochloric acid. The polymer precipitate obtained in this process was filtered off, washed with methanol and dried in a vacuum at 70° C. [158° F.]. The yield was 28 g of a polymer having a $T_g$ of 128° C. [262.4° F.].

EXAMPLE 12

Haxene Polymerization

First of all. 0.106 mmole of the chromium compound from Example 5 was dissolved in 10 mL of toluene. Then 2.64 mL of 1-hexene (21.24 mmoles) were added to this solution. The reaction mixture thus obtained was brought to a temperature of 25° C. [77° F.] and the polymerization was started by adding 300 mg of MAO (Cr:Al=1:50) dissolved in 3 mL of toluene. After a reaction time of 3 days the polymerization was interrupted by dripping the polymerization mixture into a mixture of methanol and hydrochloric acid. The yield was an oily, tacky precipitate that could not be filtered. Therefore, the methanol was distilled off once again and the resultant residue was picked up in 50 mL of cyclohexane.

Then 10 mL of water were added to this solution in order to form a lower layer for purposes of washing the obtained polymer free of chromium. Afterwards, the aqueous phase was separated out. The solvent was distilled out of the organic phase in a vacuum and the polymer residue obtained was dried in a vacuum. The yield was 3% polyhexene.

EXAMPLES 13 to 16

Norbornene Polymerization

A) Activation of the catalyst with a commercially available MAO toluene solution: First of all, 0.106 mmole of the chromium compound from Example 5 was mixed with 2 g of norbornene in 10 mL of toluene. The reaction mixture thus obtained was brought to a temperature of 25° C. (77° F.) and the reaction was started by adding 3 mL of 1.53 M methylaluminoxane solution (in toluene). After a reaction time of one hour, the reaction was interrupted by dripping the polymerization mixture into a mixture of methanol and hydrochloride acid. The resulting polymer precipitate was filtered off, washed with methanol and dried in a vacuum.

B) Activation of the catalyst with solid MAO that was picked up again in toluene: First of all, 0.106 mmole of the chromium compound from Example 5 was mixed with 2 g of norbornene dissolved in 10 mL of toluene. The reaction mixture thus obtained was brought to a temperature of 25° C. [77° F.] and the reaction was started by adding 300 mg of MAO dissolved in 3 mL of toluene. After a reaction time of one hour the reaction was interrupted by dripping the polymerization mixture into a mixture of methanol and hydrochloric acid. The resulting polymer precipitate was filtered off, washed with methanol and dried in a vacuum.

The results of the polymerizations can be seen in Table 1.

COMPARATIVE EXAMPLES 17 and 18

Norbornene Polymerization

The experiments were conducted as described above for the norbornene polymerization (B). The chromium compound from Example 4 was used in Example 17, while the chromium compound from Example 2 was employed in Example 18.

The results of the polymerizations can be found in Table 1.

TABLE 1

Results of the nnorbornene polymerization.

| Example | Metathesis[a] | Yield |
| --- | --- | --- |
| 13 (A) | no | 82% |
| 14 (B) | no | 95% |
| 15 (A) | no | 5% |
| 16 (B) | no | 53% |
| 17 (B) | yes | 89% |
| 18 (B) | yes | 5% |

[a]Metathesis refers to the product obtained from ring-opening metathesis polymerization (ROMP) (ascertained by means of NMR measurements and Tg values).

EXAMPLES 19 to 24

Ethene Polymerization

A total of 0.05 mmole of the chromium compound indicated in Table 2 was dissolved in 20 mL of toluene. The solution was transferred into a 250-mL glass autoclave, where it was first brought to a temperature of 60° C. [140° F.] and subsequently saturated with ethene for 30 minutes at 3 bar. Then the reaction was started by adding 12.5 mmoles of MAO (Cr:Al=1:250) dissolved in 20 mL of toluene. The first polymer particles already precipitated from the reaction solution after a few minutes. After a reaction time of 30 minutes at 60° C. [140° F.] under a constant ethylene pressure of 3 bar, the reaction was interrupted by dripping the polymerization mixture into 400 mL of a mixture of methanol and concentrated hydrochloric acid (10:1). The polymer precipitate obtained in this process was filtered off, washed with methanol and dried in a vacuum at 100° C. [212° F.].

Example 24 is presented for comparison purposes.

TABLE 2

Results of the ethylene polymerization.

| Example | Catalyst | Quantity [mg] | Yield [mg] | Activity [gPE/mmole · bar · h] |
| --- | --- | --- | --- | --- |
| 19 | [Cr(N$^+$Bu)Cl$_3$] | 11.5 | 287 | 3.8 |
| 20 | [Cr(N$_6$F$_5$)Cl$_3$] | 17 | 1001 | 13.4 |

TABLE 2-continued

Results of the ethylene polymerization.

| Example | Catalyst | Quantity [mg] | Yield [mg] | Activity [gPE/mmole · bar · h] |
|---|---|---|---|---|
| 21 | [Cr(NT$_8$)Cl$_3$] | 16.4 | 383 | 5.1 |
| 22 | [Cr (NBz)Cl$_3$] | 13.8 | 224 | 3 |
| 23 | [Cr (NTf)Cl$_3$] | 15.3 | 285 | 3.8 |
| 24 | [Cr (NC$_6$F$_3$)$_2$Cl$_2$] | 24.3 | 428 | 5.7 |

EXAMPLES 25 to 27

Ethene Polymerization

A total of 400 mL of toluene was placed into a one-liter autoclave at a temperature of 70° C. [158° F.], after which the amount of catalyst indicated in Table 3 was suspended in 2.5 mL of a 30%-solution of MAO (12 mmoles) and placed into the reactor after 10 minutes. The polymerization was started by pressurization with ethylene at 40 bar. After a polymerization time of one hour with ethylene at 40 bar and 70° C. [158° F.], the reaction was interrupted by relieving the pressure and the polymer was processed in the manner described above.

TABLE 3

Results of the ethylene polymerization.

| Example | Catalyst (example) | Quantity [mmole] | Hexene [mL] | Yield [g] | Activity [gP/mmole · bar · h] | η [dL/g] |
|---|---|---|---|---|---|---|
| 25 | 5 | 0.056 | — | 12 | 5.4 | 6.3 |
| 26 | 5 | 0.056 | 40 | 7 | 3.1 | 5.69 |
| 27 | 8 | 0.06 | — | 3 | 1.2 | 15.1 |

EXAMPLE 28

Ethene Polymerization

The polymerization was conducted as described above for Examples 25 to 27. The chromium complex from Example 9 was used. 2 mL of triethyl aluminum (4 mmoles) were used as the co-catalyst.

A total of 14.5 g of polyethylene having an η value of 7.8 dL/g was obtained. The activity was 3 gP/mmole·bar·h.

What is claimed is:

1. A catalyst system containing
   (A) at least one imidochromium compound, which can be obtained by a process encompassing the following process steps:
      (a) contacting a dioxochromium compound with an N-sulfinyl compound R$^1$—N=S=O or R$^2$—N=S=O, wherein the variables have the following meaning:
         R$^1$ is C$_1$–C$_{20}$-alkyl, C$_2$–C$_{20}$-alkenyl, C$_6$–C$_{20}$-aryl, alkylaryl having 1 to 10 carbon atoms in the alkyl radical and 6 to 20 carbon atoms in the aryl radical, whereby the organic radical R1 optionally have inert substituents, or SiR$^3{}_3$;
         R$^2$ is for R$^3$C=NR$^4$, R$^3$C=O, C=O(OR$^4$), R$^3$C=S, (R$^3$)$_2$P=O, (OR$^3$)$_2$P=O, SO$_2$R$^3$, R$^3$R$^4$C=N, NR$^3$R$^4$ or BR$^3$R$^4$;
         R$^3$ and R$^4$ independent of each other, are C$_1$–C$_{20}$-alkyl, C$_2$–C$_{20}$-alkenyl, C$_6$–C$_{20}$-aryl, alkylaryl having 1 to 10 carbon atoms in the alkyl radical and 6 to 20 carbon atoms in the aryl radical, hydrogen if the latter is bonded to a carbon atom, whereby the organic radicals R$^3$ and R$^4$ can also have inert substituents;
      (b) contacting the reaction product thus obtained with chlorine if a sulfinyl compound R$^1$—N=S=O was used and, in case an N-sulfinyl compound R$^2$—N=S=O was used, with chlorine of sulfurylchloride or with no other reagent;
   (B) at least one activator compound and
   (C) optionally, one or more additional catalysts.

2. The catalyst system according to claim 1, in which the Imidochromium compound can be obtained by contacting dioxochromium dichloride with the N-sulfinyl compound.

3. The catalyst system according to claim 1, in which the Imidochromium compounds having the general formula I,

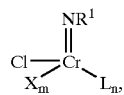

are used, wherein the variables have the following meaning:
   X independent of each other, stands for fluorine, chlorine, bromine, iodine, NR$^5$R$^6$, NP(R$^5$)$_3$, OR$^5$, OSi(R$^5$)$_3$, SO$_3$R$^5$, OC(O)R$^5$, β-diketonate, sulfate, dicarboxylates dialcoholates, BF$_4{}^-$, PF$_6{}^-$, or bulky weakly or non-coordinating anions;
   R$^1$ stands for C$_1$–C$_{20}$-alkyl, C$_2$–C$_{20}$-alkenyl, C$_6$–C$_{20}$-aryl, alkylaryl having 1 to 10 carbon atoms in the alkyl radical and 6 to 20 carbon atoms in the aryl radical, whereby the organic radical R$^1$ can also have inert substituents, or SiR$^3{}_3$;
   R$^3$, R$^5$, R$^6$ independent of each other, stand for C$_1$–C$_{20}$-alkyl, C$_2$–C$_{20}$-alkenyl, C$_6$–C$_{20}$-aryl, alkylaryl having 1 to 10 carbon atoms in the alkyl radical and 6 to 20 carbon atoms in the aryl radical, for hydrogen if the latter is bonded to a carbon atom, whereby the organic radicals R$^3$, R$^5$ and R$^6$ can also have inert substituents;
   L is a neutral donor;
   n is 0 to 3;
   m is 1 for dianionic X, 2 for monoanionic X.

4. The catalyst system according to claim 1, wherein the activator compound (B) is selected from the group consisting of aluminoxane, trimethyl aluminum, triethyl aluminum, triisobutyl aluminum, dimethyl aluminum chloride, diethyl aluminum chloride, methyl aluminum dichloride, ethyl aluminum chloride, methyl aluminum sesquichloride, dimethyl anilinium tetrakispentafluorophenyl borate, trityltetrakispentafluorophenyl borate and trispentafluorophenyl borane.

5. A process for the polymerization of olefins at temperatures within the range from 0° C. to 300° C. and at pressures ranging from 1 bar to 4000 bar, which comprises carrying out the polymerization is in the presence of the catalyst system according to claim 1.

6. The process according to claim 5, wherein the polymerization is carried out in the gas phase, solution or suspension.

7. The process according to claim 5, wherein at least one olefin selected from the group consisting of ethene, propene, 1-butene, 1-pentene, 1-hexene, 1-heptene, 1-octene, cyclopentene and norbornene is polymerized.

8. The process according to claim 5, wherein said catalyst system is immobilized on a support.

* * * * *

UNITED STATES PATENT AND TRADEMARK OFFICE
CERTIFICATE OF CORRECTION

PATENT NO.    : 6,784,261 B1  Page 1 of 1
DATED         : August 31, 2004
INVENTOR(S)   : Marcus Schopf et al.

It is certified that error appears in the above-identified patent and that said Letters Patent is hereby corrected as shown below:

<u>Title page,</u>
Item [75], Inventors, "Jennifer Kiepke" should read -- Jennifer Kipke --.

Signed and Sealed this

Fourteenth Day of December, 2004

JON W. DUDAS
*Director of the United States Patent and Trademark Office*